United States Patent [19]

Mignani et al.

[11] Patent Number: 4,705,650
[45] Date of Patent: Nov. 10, 1987

[54] PROCESS FOR THE PREPARATION OF COMPOUNDS HALOGENATED α TO AN ELECTRON-ATTRACTING GROUP

[75] Inventors: Gerard Mignani, Lyons; Didier Morel, Villiers sur Orge, both of France

[73] Assignee: Rhone-Poulenc Sante, Courbevoie, France

[21] Appl. No.: 753,532

[22] Filed: Jul. 10, 1985

[30] Foreign Application Priority Data

Jul. 12, 1984 [FR] France ................... 84 11087

[51] Int. Cl.[4] ............................................. C07C 147/06
[52] U.S. Cl. ................... 260/405.5; 260/408;
558/388; 558/438; 558/440; 558/441; 558/442;
558/443; 558/445; 558/454; 558/457; 558/460;
560/51; 560/81; 560/111; 560/150; 560/156;
560/172; 560/174; 560/177; 560/192; 560/205;
560/219; 560/226; 564/172; 564/182; 564/199;
564/209; 568/28; 564/204; 568/306; 568/307;
568/316; 568/393; 568/433; 568/459; 568/466;
568/928; 568/936; 568/946
[58] Field of Search .................... 260/405.5, 408;
560/226, 192, 219, 111, 205, 174, 51, 156, 150,
172, 177, 81; 568/28, 393, 316, 433, 306, 307,
459, 466, 946, 928, 936; 564/172, 199, 182, 204,
209; 558/388, 438, 440, 441, 442, 443, 445, 454,
457, 460

[56] References Cited
FOREIGN PATENT DOCUMENTS 0082781 6/1983 European Pat. Off. .

OTHER PUBLICATIONS

Boatman et al., *J. Org. Chem.*, vol. 30, pp. 3321-3324, (1965).
Stotter et al., *Tetrahedron Letters*, 1972, No. 40, pp. 4067-4070.

*Organic Syntheses*, pp. 766-771.
Otto Isler, "Bitamina A e carotenoidi(*)" vol. 49, No. 12—Dec. 1967, pp. 1317–1332.

*Primary Examiner*—Donald B. Moyer
*Assistant Examiner*—Bruce D. Gray
*Attorney, Agent, or Firm*—Stevens, Davis, Miller & Mosher

[57] ABSTRACT

Compounds halogenated in the α-position to an electron-attracting group of formula

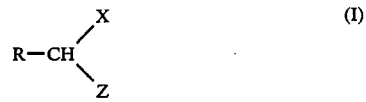
(I)

in which X denotes a halogen atom, R denotes a hydrogen atom or a hydrocarbon radical or a radical —(CH$_2$)$_3$—COOR$_1$ and Z denotes a radical —CHO, —COR$_2$, —COOR$_3$, —CONR$_4$R$_5$, —CN, —SO$_2$R$_6$, —NO$_2$, —CO—(CH$_2$)p—COO$_1$ or —COO(CH$_2$)p—COOR$_1$ are made by a halogenating deacylation of a compound of formula

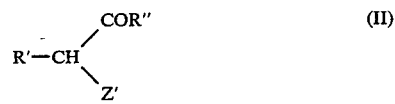
(II)

in which R' denotes a hydrogen atom or a hydrocarbon radical, R" denotes a methyl radical and Z' denotes a radical —CHO, —COR$_2$, —COOR$_3$, —CONR$_4$R$_5$, —CN, —SO$_2$R$_6$ or —NO$_2$ or R' and R" may form a radical —(CH$_2$)— or R' and R" may form a radical —CO—(CH$_2$)p— or —COO(CH$_2$)p—, using an alkali metal alcoholate or an alkali or alkaline-earth metal carbonate and a halogenating agent.

7 Claims, No Drawings

PROCESS FOR THE PREPARATION OF COMPOUNDS HALOGENATED α TO AN ELECTRON-ATTRACTING GROUP

The present invention provides a process for the preparation of compounds halogenated in an α-position to an electron-attracting group and of the formula:

in which:

X denotes a halogen atom, preferably a chlorine or bromine atom,

R denotes a hydrogen atom or a saturated hydrocarbon radical or an unsaturated hydrocarbon radical containing one or more double or triple bonds, these radicals being unsubstituted or substituted by one or more radicals, which are identical or different, chosen from phenyl, alkoxycarbonyl, acyl and cyano radicals, and Z denotes a radical —CHO, —COR$_2$, COOR$_3$, —CONR$_4$R$_5$, —CN, —SO$_2$R$_6$, —NO$_2$, —CO—O(CH$_2$)p—COOR$_1$ or —CO—(CH$_2$)p—COOR$_1$, p being an integer from 2 to 10 inclusive, it being understood that Z cannot denote —CO—(CH$_2$)p—COOR$_1$ or —CO—O—(CH$_2$)p—COOR$_1$, when R is a radical —(CH$_2$)$_n$COOR$_1$, in which n is an integer of from 3 to 10 inclusive, which comprises simultaneously halogenating and deacylating a compound of the formula:

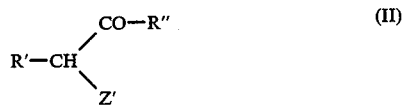

in which

R' denotes a hydrogen atom or a saturated hydrocarbon radical or an unsaturated hydrocarbon radical containing one or more double or triple bonds, these radicals being unsubstituted or substituted by one or more radicals, which are identical or different, chosen from phenyl, alkoxycarbonyl, acyl and cyano radicals R" denotes a methyl radical Z' denotes a radical —CHO, —COR$_2$, —COOR$_3$, —CONR$_4$R$_5$, —CN, —SO$_2$R$_6$ and —NO$_2$, it being understood that R' and R" may together form a radical —(CH$_2$)$_n$— in which n is as hereinbefore defined or that R" and Z' may together form a radical —CO(CH$_2$)p— or —CO—O—(CH$_2$)p— in which p is as hereinbefore defined, the aforesaid saturated hydrocarbon radicals containing 1 to 20 carbon atoms each, the said unsaturated hydrocarbon radicals containing 2 to 20 carbon atoms each, and the radicals R$_1$, R$_2$, R$_3$, R$_4$, R$_5$ and R$_6$ each denote alkyl radicals containing 1 to 4 carbon atoms each and the alkyl moieties of the alkoxycarbonyl radicals contain 1 to 4 carbon atoms each, by treatment with an alkali metal alcoholate or an alkali metal or alkaline earth metal carbonate in an organic solvent and a halogenating agent at a temperature of from —30° to 100° C.

It is known, in particular according to P. L. Stotter and K. A. Hill, Tetrahedron Letters, 40, 4067-4070 (1972), to prepare α-bromo esters by deacylation, using anhydrous barium hydroxide in an alcohol, of a bromo-keto ester produced by the reaction of bromine with the enolate of the β-keto ester.

Furthermore, it is known that the deacylation of diacetylated compounds may be carried out by heating in a basic alcoholic medium, as described, for example, by S. Boatman et al., J. Org. Chem., 30, 3321 (1965) or by S. Boatman and C. R. Hauser, Organic Syntheses, Coll. Vol. V, 767 (1973).

It is also known that heating a β-keto ester in the presence of an alkali metal alcoholate (sodium methylate) in an alcohol (methanol) results in a deacylation reaction.

The present invention is based on the discovery that when a compound of formula (II) is treated with an alkali metal alcoholate or with an alkali or alkaline-earth metal carbonate in an organic solvent and with a halogenating agent at a temperature of between —30° and +100° C., a product of formula (I) is obtained by a simultaneous deacylation and halogenation reaction.

To make use of the process according to the invention it is particularly advantageous to employ an alkali metal alcoholate derived from an alcohol of general formula R$_1$OH (III), in which R$_1$ is defined as previously, such as sodium methylate or ethylate in the corresponding alcohol. The use of sodium methylate is particularly advantageous in order to avoid transesterification reactions. However, good results are obtained by using an alcohol of general formula (III) in the presence of sodium hydroxide or potassium hydroxide.

It is possible to employ the alkali metal alcoholate in an anhydrous organic solvent such as toluene, ethyl ether, dimethylformamide or N-methylpyrrolidone.

It is also possible to employ an alkali or alkaline-earth metal carbonate in an organic solvent such as acetone or acetonitrile.

In general, one mole of an alkali metal alcoholate or an alkali or alkaline-earth metal carbonate is employed per mole of product of general formula (II) which is used.

The halogenating agents which are particularly suitable are chosen, preferably, from molecular halogens (chlorine, bromine), N-halosuccinimides, sulphuryl chloride and hexachloroethane.

In general, a quantity of halogenating agent which is slightly greater than the stoichiometric amount is employed.

It should be made clear that, according to the process of the present invention, the compounds of formula (I) in which R denotes a radical —(CH$_2$)$_n$—COOR$_1$ are obtained from the compounds of formula (II) in R' and R" together from a radical —(CH$_2$)$_n$— in which n is an integer from 3 to 10 inclusive, and that the compounds of formula (I) in which Z denotes a radical —CO—(CH$_2$)p—COOR$_1$ or —CO—O—(CH$_2$)p—COOR$_1$ are obtained from the compounds of formula (II) in which Z and R" together form a radical —CO—(CH$_2$)p— or —CO—O—(CH$_2$)p— in which p is an integer from 2 to 10 inclusive, by reaction with an alkali metal alcoholate derived from an alcohol of the formula (III) and a halogenating agent.

It should also be made clear that when R" denotes a methyl radical in the compound of formula (II), there is formed, besides the product of formula (I), also an ester of formula:

$$CH_3COOR_1 \quad (IV)$$

in which $R_1$ is as previously defined.

The compounds of formula (I) produced by the process of the present invention may be isolated from the reaction mixture by the usual extraction methods and may be purified by the application of physico-chemical methods such as distillation or chromatography.

The compounds of formula (I) are of particular interest as intermediates in organic chemistry. For example, the compounds of formula (I) in which Z denotes a radical —$COR_2$ can readily give pseudoionone, which is an intermediate which can be used in the synthesis of vitamin A.

Pseudoionone may be obtained by dehydrohalogenation of the compound of formula:

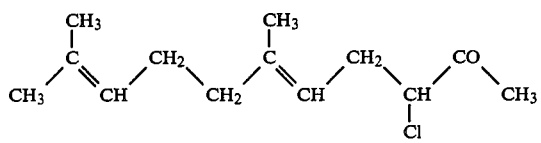

and/or

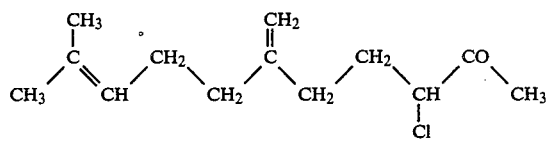

using lithium chloride in a basic polar aprotic solvent such as N-methylpyrrolidone at a temperature of between 80° and 160° C. for 1 to 20 hours.

The following Examples show how the invention may be applied in practice.

EXAMPLE 1

Methanol (100 cc) and, in small portions, sodium (1.39 g; 60.4 milligram-atoms) are introduced, under an argon atmosphere, into a 250 cc three-necked round flask. After cooling to −35° C. a 55/45 mixture of:

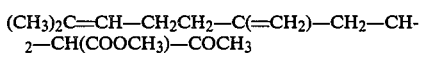

and

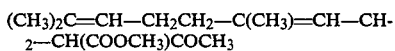

(15.24 g; 60.4 millimoles) is added, followed by N-chlorosuccinimide (8.17 g; 61 millimoles). The temperature is allowed to return to 25° C. and then is maintained at this value for 6 hours. The reaction mixture is taken up with water (100 cc) and then extracted with ethyl ether (4×50 cc). The combined organic phases are dried over sodium sulphate. After filtration and evaporation of the solvent a colourless oil (13.65 g) is obtained which, after distillation under reduced pressure (0.8 mm Hg; 0.11 kPa) at 102° C., yields a 55/45 mixture of:

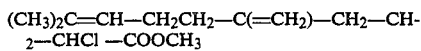

and

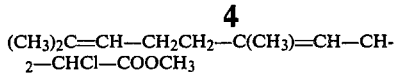

(9.31 g).

The yield of isolated product is 63.5%.

An assay of the crude reaction product by gas phase chromatography, with an internal standard, shows that the conversion of the starting ester is 100% and that the yield of chlorinated compounds is 72%.

The structure of the products obtained is confirmed by the infrared spectrum, the mass spectrum and the proton nuclear magnetic resonance spectrum.

EXAMPLE 2

Anhydrous methanol (50 cc) and, in small portions, sodium (0.69 g; 30 milligram-atoms) are introduced, under an argon atmosphere, into a 100 cc three-necked round flask. After cooling to −35° C., a 55/45 mixture of:

and

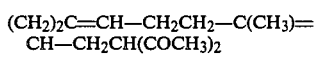

and (6.77 g; 28.7 millimoles) is added, followed by N-chlorosuccinimide (4.08 g; 30 millimoles). The temperature is allowed to return to 25° C. and then the reaction mixture is stirred at this temperature for 5 hours 30 minutes. The reaction mixture is taken up with water (100 cc) and then extracted with ethyl ether (4×50 cc). The combined organic phases are dried over sodium sulphate. After filtration and evaporation of the solvent a yellow oil (6.9 g) is obtained which, after distillation under reduced pressure (0.9 mm Hg; 0.12 kPa) at 91°–92° C., yields a 55/45 mixture of:

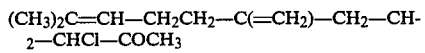

and

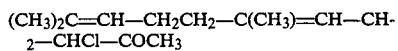

(4.19 g).

The yield of isolated product is 64%.

An assay of the crude reaction product by gas phase chromatography with an internal standard, shows that the conversion of the initial β-diketone is in the region of 100% and that the yield of chlorinated compounds is 84%.

The structure of the products obtained is confirmed by the infrared spectrum, the mass spectrum and the proton nuclear magnetic resonance spectrum.

EXAMPLE 3

Anhydrous methanol (15 cc) and, in small portions, sodium (0.206 g; 8.9 milligram-atoms) are introduced, under an argon atmosphere, into a 100 cc three-necked round flask. After cooling to −35° C., a 55/45 mixture of:

and

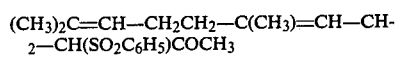
(CH$_3$)$_2$C=CH—CH$_2$CH$_2$—C(CH$_3$)=CH—CH$_2$—CH(SO$_2$C$_6$H$_5$)COCH$_3$ (3.0 g; 9 millimoles) is added, followed by N-chlorosuccinimide (1.22 g; 9.1 millimoles). The temperature is allowed to return to 25° C. and then the reaction mixture is stirred at this temperature for 16 hours. The reaction mixture is taken up with water (100 cc) and extracted with ethyl ether (4×50 cc). The combined organic phases are dried over sodium sulphate. After filtration and evaporation of the solvent a yellow oil (2.78 g) is obtained, analysis of which by proton nuclear magnetic resonance shows that it contains 90% of a 55/45 mixture of:

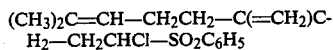
(CH$_3$)$_2$C=CH—CH$_2$CH$_2$—C(=CH$_2$)CH$_2$—CH$_2$CHCl—SO$_2$C$_6$H$_5$ and

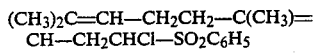
(CH$_3$)$_2$C=CH—CH$_2$CH$_2$—C(CH$_3$)=CH—CH$_2$CHCl—SO$_2$C$_6$H$_5$ The yield of isolated product is 85%.

The structure of the products obtained is confirmed by the infrared spectrum, the mass spectrum and the proton nuclear magnetic resonance spectrum.

EXAMPLE 4

Anhydrous methanol (50 cc) and, in small portions, sodium (0.7 g; 30 milligram-atoms) are introduced, under an argon atmosphere, into a 100 cc three-necked round flask. After cooling to −35° C., a 55/45 mixture of:

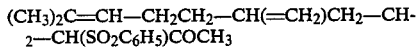
(CH$_3$)$_2$C=CH—CH$_2$CH$_2$—CH(=CH$_2$)CH$_2$—CH$_2$—CH(SO$_2$C$_6$H$_5$)COCH$_3$ and

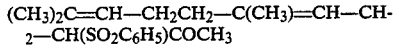
(CH$_3$)$_2$C=CH—CH$_2$CH$_2$—C(CH$_3$)=CH—CH$_2$—CH(SO$_2$C$_6$H$_5$)COCH$_3$ (10.03 g; 30 millimoles) is added, followed by N-bromosuccinimide (5.31 g; 30 millimoles). The temperature is allowed to return to 25° C. and then the reaction mixture is stirred at this temperature for 16 hours. The reaction mixture is taken up with water (100 cc) and extracted with ethyl ether (4×50 cc). The combined organic phases are dried over sodium sulphate. After filtration and evaporation of the solvent, an oil (10.55 g) is obtained, the analysis of which by proton nuclear magnetic resonance shows that it consists of a 55/45 mixture of:

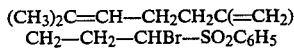
(CH$_3$)$_2$C=CH—CH$_2$CH$_2$C(=CH$_2$)CH$_2$—CH$_2$—CHBr—SO$_2$C$_6$H$_5$ and

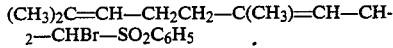
(CH$_3$)$_2$C=CH—CH$_2$CH$_2$—C(CH$_3$)=CH—CH$_2$—CHBr—SO$_2$C$_6$H$_5$ .

The yield of isolated product is 95%.

The structure of the products obtained is confirmed by the infrared spectrum, the mass spectrum and the proton nuclear magnetic resonance spectrum.

EXAMPLE 5

Methanol (50 cc) and, in small portions, sodium (0.79 g; 34.4 milligram-atoms) are introduced, under an argon atmosphere, into a 100 cc three-necked round flask. After cooling to −35° C., a 55/45 mixture of:

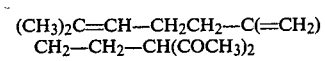
(CH$_3$)$_2$C=CH—CH$_2$CH$_2$—C(=CH$_2$)CH$_2$—CH$_2$—CH(COCH$_3$)$_2$ and

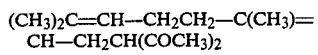
(CH$_3$)$_2$C=CH—CH$_2$CH$_2$—C(CH$_3$)=CH—CH$_2$CH(COCH$_3$)$_2$ (7.74 g; 33 millimoles) is added, followed by N-chlorosuccinimide (4.41 g; 33 millimoles). The temperature is allowed to return to 25° C. and then the reaction mixture is stirred at this temperature for 16 hours. The reaction mixture is taken up with water (100 cc) and then extracted with ethyl ether (2×50 cc). The combined organic phases are dried over sodium sulphate. After filtration and evaporation of the solvent, a 55/45 mixture of:

(CH$_3$)$_2$C=CHCH$_2$CH$_2$—C(=CH$_2$)CH$_2$—CH$_2$CHCl—COCH$_3$ and (CH$_3$)$_2$C=CH—CH$_2$CH$_2$—C(CH$_3$)=CH—CH$_2$—CHCl—COCH$_3$ (5.3 g; 23 millimoles) is obtained.

The yield of isolated product is 70%.

The initial β-diketone, in the form of a 55/45 mixture, may be prepared in the following manner:

Into a 125 cc stainless steel autoclave are introduced, under an argon atmosphere: a water-methanol mixture (75-25 by volume; 20 cc), sodium carbonate (0.302 g), tri(m-sulphophenyl)phosphine in the form of a sodium salt (0.833 g), [RhCl(1,5-cyclooctadiene)]$_2$ (0.0686, i.e. 0.0027 milligram-atom of rhodium), acetylacetone (8.01 g; 80 millimoles) and myrcene (16.4 g; 120.6 millimoles). The mixture is allowed to react at 90° C. for 16 hours.

After cooling, ethyl ether (40 cc) is added and the reaction mixture is transferred to a separating funnel. The aqueous phase, which is separated off by gravity, is extracted with ethyl ether (25 cc). The combined organic phases are dried over sodium sulphate. After filtration and evaporation of the solvent, an orange oil (21.73 g) is obtained, containing a 55/45 mixture of:

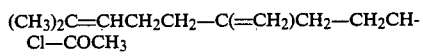
(CH$_3$)$_2$C=CH—CH$_2$CH$_3$—C(=CH$_2$)CH$_2$—CH$_2$—CH(COCH$_3$)$_2$ and

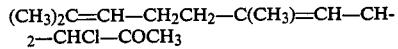
(CH$_3$)$_2$C=CH—CH$_2$CH$_2$—C(CH$_3$)=CH—CH$_2$—CH(COCH$_3$)$_2$ (15.21 g).

The yield of isolated product is 80.6%.

EXAMPLE 6

Anhydrous methanol (30 cc) and, in small portions, sodium (0.69 g; 30 milligram-atoms) are introduced, under an argon atmosphere, into a 100 cc three-necked round flask. After cooling to −35° C.,

(5.16 g; 30 millimoles) is added, followed by N-chlorosuccinimide (4.0 g; 30 millimoles). The temperature is allowed to return to 25° C. and then the reaction mixture is stirred at this temperature for 18 hours. The reaction mixture is taken up with water (100 cc) and ethyl ether (100 cc). The aqueous phase, separated off by gravity, is extracted with ether (3×50 cc). The combined organic phases are dried over sodium sulphate. After filtration and evaporation of the solvent, a colourless oil is obtained which, after a flash-distillation at 100° C. at a pressure of 1 mm Hg (0.13 kPa) yields a colourless oil (3.2 g) containing 95% of

The yield of isolated product is 62%.

The structure of the product obtained is confirmed by the infrared spectrum, the mass spectrum and the proton nuclear magnetic resonance spectrum.

EXAMPLE 7

Anhydrous ethanol (30 cc) and, in small portions, sodium (0.69 g; 30 milligram-atoms) are introduced, under an argon atmosphere, into a 100 cc three-necked round flask. After cooling to −30° C., 2-ethoxycarbonylcyclohexanone (5.1 g; 30 millimoles) and N-chlorosuccinimide (4.0 g; 30 millimoles) are added. The temperature is allowed to return to 25° C. and then the reaction mixture is stirred at this temperature for 10 hours. The reaction mixture is taken up with water (100 cc) and ethyl ether (100 cc). After gravity separation, the aqueous phase is extracted with ethyl ether (3×30 cc). The combined organic phases are dried over sodium sulphate. After filtration and evaporation of the solvent a yellow oil (7.7 g) is obtained which, after a flash-distillation at 200° C. at a pressure of 1 mm Hg (0.13 kPa) yields a colourless oil (3.6 g) containing 90% of 1,5-diethoxycarbonyl-1-chloropentane.

The structure of the product obtained is confirmed by the infrared spectrum, the mass spectrum and the proton nuclear magnetic resonance spectrum.

EXAMPLE 8

Methanol (30 cc) and, in small portions, sodium (0.69 g; 30 milligram-atoms) are introduced, under an argon atmosphere, into a 100 cc three-necked round flask. After cooling to −30° C., a 60/40 mixture of:

and

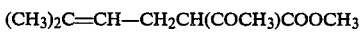

(5.52 g; 30 millimoles) and N-chlorosuccinimide (4.0 g; 30 millimoles) are added. The temperature is allowed to return to 25° C. and then the reaction mixture is stirred at this temperature for 10 hours. The reaction mixture is taken up with water (100 cc) and ethyl ether (100 cc). After gravity separation, the aqueous phase is extracted with ethyl ether (3×30 cc). The combined organic phases are dried over sodium sulphate. After filtration and evaporation of the solvent a yellow oil (5.7 g) is obtained which, after a flash-distillation at 150° C. at a pressure of 20 mm Hg (2.6 kPa) yields a colourless oil (3.5 g) containing a 60/40 mixture of:

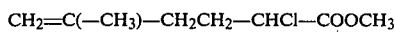

and

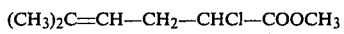

The yield of isolated product is 66%.

The structure of the products obtained is confirmed by the infrared spectrum, the mass spectrum and the proton nuclear magnetic resonance spectrum.

EXAMPLE 9

Methanol (30 cc) and, in small portions, sodium (0.46 g) (20 milligram-atoms) are introduced, under an argon atmosphere, into a 100 cc three-necked round flask. After cooling to −30° C. a 55/45 mixture of:

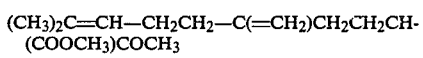

and

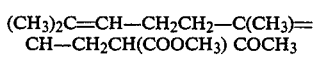

(5.04 g; 30 millimoles) is added, followed by N-bromosuccinimide (3.56 g; 20 millimoles). The temperature is allowed to return to 25° C. and then the reaction mixture is stirred at this temperature for 10 hours. At the end of reaction the reaction mixture is homogeneous and light yellow. The reaction mixture is taken up with water (100 cc) and ethyl ether (100 cc). After gravity separation the aqueous phase is extracted with ether (3×30 cc). The combined organic phases are dried over sodium sulphate. After filtration and evaporation of the solvent a yellow oil (5.1 g) is obtained which, after flash-distillation at 200° C. at a pressure of 1 mm Hg (0.13 kPa), yields a colourless oil (3.5 g) containing 85% of a 55/45 mixture of:

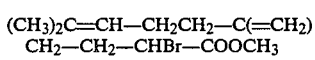

and

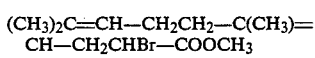

The structure of the products obtained is confirmed by the infrared spectra, the mass spectrum and the proton nuclear magnetic resonance spectrum.

EXAMPLE 10

Anhydrous methanol (30 cc) and, in small portions, sodium (0.69 g; 30 milligram-atoms) are introduced, under an argon atmosphere, into a 100 cc three-necked round flask. After cooling to −20° C., a 60/40 mixture of:

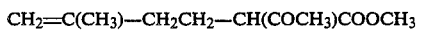

and

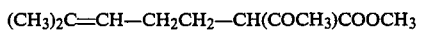

(5.52 g; 30 millimoles) and N-bromosuccinimide (5.33 g; 30 millimoles) are added. The temperature is allowed to return to 25° C. and then the reaction mixture is stirred at this temperature for 10 hours. The reaction mixture is taken up with water (100 cc) and anhydrous ether (100 cc). After gravity separation, the aqueous phase is extracted with ethyl ether (3×30 cc). The combined organic phases are dried over sodium sulphate. After filtration and evaporation of the solvent a yellow oil (6.1 g) is obtained which, after a flash distillation, yields a colourless oil (3.9 g).

Analysis by proton nuclear magnetic resonance shows that the crude reaction product consists of 85% of a mixture of:

$$CH_2=C(CH_3)CH_2CH_2-CHBr-COOCH_3$$

and $$(CH_3)_2C=CH-CH_2CH_2-CHBr-COOCH_3$$

and 15% of the initial β-keto esters.

The structure of the products obtained is confirmed by the infrared spectrum, the mass spectrum and the proton nuclear magnetic resonance spectrum.

EXAMPLE 11

Anhydrous methanol (25 cc) and, in small portions, sodium (0.45 g; 19.5 milligram-atoms) are introduced, under an argon atmosphere, into a 100 cc three-necked round flask. A 55/45 mixture of:

$$(CH_3)_2C=CH-CH_2CH_2C(=CH_2)CH_2CH_2-CH((COCH_3)COOCH_3$$

and $$(CH_3)_2C=CH-CH_2CH_2-C(CH_3)=CH-CH_2CH(COCH_3)COOCH_3,$$

(5.92 g; 23.5 millimoles) is then added and then the mixture is cooled to a temperature between 5° and 8° C. A solution of chlorine (1.7 g; 24 millimoles) in carbon tetrachloride (20 cc) is added. The reaction mixture is stirred at 5° C. for 5 hours. The reaction mixture is taken up with water (100 cc) and ethyl ether (100 cc). After gravity separation, the aqueous phase is extracted with ethyl ether. The combined organic phases are dried over sodium sulphate. After filtration and evaporation of the solvent, a crude reaction product is obtained which contains 30% of a 55/45 mixture of:

$$(CH_3)_2C=CH-CH_2CH_2-C(=CH_2)-CH_2CH_2-CHCl-COOCH_3$$

$$(CH_3)_2C=CH-CH_2CH_2-C(CH_3)=CH_2-CH_2CHCl-COOCH_3$$

EXAMPLE 12

Anhydrous methanol (20 cc) and, in small portions, sodium (0.23 g) (10 milligram-atoms) are introduced, under an argon atmosphere, into a 100 cc three-necked round flask and then a 55/45 mixture of:

$$(CH_3)_2C=CH-CH_2CH_2-C(=CH_2)CH_2CH_2CH-(COCH_3)COOCH_3$$

and $$(CH_3)_2C=CH-CH_2CH_2-C(CH_3)=CHCH_2CH-(COCH_3)COOCH_3,$$

(2.52 g; 10 millimoles) is added, followed, slowly, by sulphuryl chloride (0.8 cc; 10 millimoles) at a temperature in the region of 20° C. The materials are left to react for 6 hours. The reaction mixture is taken up with water (100 cc) and ethyl ether (100 cc). After gravity separation the aqueous phase is extracted with ethyl ether (3×30 cc). The combined organic phases are dried over sodium sulphate. After filtration and evaporation of the solvent a colourless oil (2.6 g) is obtained.

Analysis by vapour phase chromatography shows that the crude reaction product contains 45% of initial β-keto esters and 50% of a mixture of:

$$(CH_3)_2C=CH-CH_2CH_2-C(=CH_2)CH_2CH_2-CHCl-COOCH_3$$

and $$(CH_3)_2C=CH-CH_2CH_2-C(CH_3)=CH-CH_2-CHCl-COOCH_3$$

EXAMPLE 13

Methanol (20 cc), ground potassium hydroxide (0.56 g; 0.02 mole) and a 55/45 mixture of:

$$(CH_3)_2C=CH-CH_2CH_2-C(=CH_2)-CH_2CH_2-CH(COOCH_3)COCH_3$$

and $$(CH_3)_2C=CH-CH_2CH_2-C(CH_3)=CH-CH_2-CH(COOCH_3)COCH_3$$

(2.52 g; 0.01 mole) are introduced, under an argon atmosphere, into a 100 cc round flask.

N-chlorosuccinimide (1.4 g; 0.0104 mole) is then added and the mixture is left to react at 25° C. for 2 hours. The solution become homogeneous. The reaction mixture is taken up with water (100 cc) and extracted with ether (3×50 cc). The organic phases are combined and dried over magnesium sulphate. After filtration and evaporation of the solvent a slightly yellow oil is obtained, which contains 70% of a 55/45 mixture of:

$$(CH_3)_2C=CH-CH_2CH_2-C(=CH_2)-CH_2CH_2-CHCl-COOCH_3$$

and $$(CH_3)_2C=CH-CH_2CH_2-C(CH_3)=CH-CH_2-CHCl-COOCH_3$$

After a flash-distillation a mixture (2.0 g) of the chlorinated compounds is obtained, with a purity of 93%.

The yield of isolated product is 76%.

EXAMPLE 14

Preparation of pseudoionone 2,4,6-Trimethylpyridine (1.29 g; 10.6 millimoles) and the mixture of products obtained in Example 5 (1.94 g) are added to lithium chloride (0.5 g; 11.7 millimoles) in N-methylpyrrolidone (20 cc).

The mixture is heated at 150° C. for 2 hours and 30 minutes. After treatment of the reaction mixture, pseudoionone (1.44 g) is obtained, with a yield of 88%.

The selectivity for pseudoionone is 94.6% at a degree of dehydrochlorination of 93%.

EXAMPLE 15

Acetone (20 cc), potassium carbonate (2.76 g; 0.02 mole), hexachloroethane (4.73 g; 0.02 mole) and a 55/45 mixture of:

$(CH_3)_2C=CH-CH_2CH_2-C(=CH_2)$
$CH_2CH_2-CH(COCH_3)-COOCH_3$ and $(CH_3)_2C=CH-CH_2CH_2-C(CH_3)=CH-CH_2-CH(COCH_3)-COOCH_3$ (2.53 g; 0.01 mole) are introduced, under an argon atmosphere, into a 100 cc round flask.

The heterogeneous reaction mixture is heated under reflux for 75 hours. After cooling, the reaction mixture is filtered and then taken up with water (100 cc). After extraction with pentane (3×50 cc), the combined organic layers are dried over sodium sulphate. After filtration, evaporation of the solvent and flash chromatography, a 55/45 mixture of:

$(CH_3)_2C=CH-CH_2CH_2-C(=CH_2)CH_2CH_2-C-Cl-COOCH_3$ and $(CH_3)_2C=CH-CH_2CH_2-C(CH_3)=CH-CH_2-CCl-COOCH_3$ (1.86 g) is isolated.

The yield of isolated product is 76%.

EXAMPLE 16

Anhydrous ethanol (40 cc) and sodium (0.45 g) are introduced, under an argon atmosphere into a 100 cc round flask. When the reaction has ended, ethyl 3-phenyl-2-acetylpropionate $[C_6H_5-CH_2-CH(COCH_3)-COOC_2H_5]$ (4.3 g; 19.5 millimoles) and N-chlorosuccinimide (2.7 g; 20.2 millimoles) are added. The mixture is left to react at a temperature in the region of 20° C. for 3 hours. The reaction mixture is poured into water (100 cc) and then extracted with hexane (3×50 cc). The combined organic phases are dried over sodium sulphate. After filtration and evaporation of the solvent a pale yellow oil (3.66 g) is obtained, whose analysis by gas phase chromatography shows that it contains 98% of ethyl 3-phenyl-2-chloropropionate $[C_6H_5-CH_2CHCl-COOC_2H_5]$.

The yield is 86%.

The structure of the product obtained is confirmed by the infrared spectrum, the proton nuclear magnetic resonance spectrum and the mass spectrum.

Ethyl 3-phenyl-2-chloropropionate thus obtained may be converted to phenylalanine using known methods.

EXAMPLE 17

Anhydrous ethanol (50 cc) and lithium (0.18 g) are introduced, under an argon atmosphere, into a 100 cc round flask. They are left to react and then ethyl 3-phenyl-2-acetylpropionate (4.2 g; 19 millimoles) is added, followed by N-bromosuccinimide (4.6 g; 25.8 millimoles). The mixture is left to react at a temperature in the region of 20° C. for 1 hour. The reaction mixture is taken up with water (100 cc) and the pH is adjusted to 1. The mixture is then extracted with hexane (3×50 cc). The combined organic phases are dried over sodium sulphate. After filtration and evaporation of the solvent a slightly yellow oil (4.91 g) is obtained, whose analysis by gas phase chromatography shows that it contains 93% of ethyl 3-phenyl-2-bromopropionate.

The yield is 93%.

The structure of the product obtained is confirmed by the infrared spectrum, the proton nuclear magnetic resonance spectrum and the mass spectrum.

EXAMPLE 18

Anhydrous ethanol (50 cc) and Lithium (0.26 g) are introduced, under an argon atmosphere, into a 100 cc round flask. They are left to react and then ethyl round flask. They are left to react and then ethyl 3-methyl-2-acetylbutanoate $[(CH_3)_2CH-CH(COCH_3COOC_2H_5]$ (4.13 g; 24 millimoles) and N-chlorosuccinimide (4.98 g; 37.3 millimoles) are added. The materials are left to react at a temperature in the region of 20° C. for 3 hours. The reaction mixture is taken up with water (100 cc) and the pH is adjusted to 1. The mixture is then extracted with hexane (3×50 cc). The combined organic phases are dried over sodium sulphate. After filtration and evaporation of the solvent a slightly yellow oil (3.7 g) is obtained, whose analysis by gas phase chromatography shows that it contains 82% of ethyl 3-methyl-2-chlorobutanoate $[(CH_3)_2CH-CHCL-COOC_2H_5]$.

The yield is 77%.

The structure of the product obtained is confirmed by the infrared spectrum, the proton nuclear magnetic resonance spectrum and the mass spectrum.

We claim:

1. A process for the preparation of a compound halogenated in an α-position to an electron-attracting group and of the formula:

$$R-CH\begin{matrix}X\\Z\end{matrix}$$

in which

X denotes a halogen atom;

R denotes
  a hydrogen atom, or
  a saturated hydrocarbon radical, or
  an unsaturated hydrocarbon radical containing one or more double or triple bonds,
  these radicals being unsubstituted or substituted by one or more radicals, which are identical or different, chosen from
    phenyl,
    alkoxy-carbonyl,
    acyl, and
    cyano radicals; and Z denotes a radical —CHO, —COR$_2$, —COOR$_3$, —CONR$_4$R$_5$, —CN, —SO$_2$R$_6$, —NO$_2$, —CO—(CH$_2$)p—COOR$_1$ or —CO—O(CH$_2$)$_p$—COOR$_1$, p being an integer from 2 to 10 inclusive, the radical Z not denoting —CO(CH$_2$)$_p$—COOR$_1$ or —CO—O(CH$_2$)$_p$—COOR$_1$ when R is a said saturated hydrocarbon radical substituted by alkoxy-carbonyl and of formula —(CH$_2$)$_n$—COOR$_1$ in which n is an integer from 3 to 10;

which process comprises simultaneously halogenating and deacylating a compound of the formula:

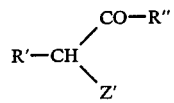

in which
R' denotes
a hydrogen atom or
a saturated hydrocarbon radical or
an unsaturated hydrocarbon radical containing one or
more double or triple bonds,
these radicals being unsubstituted or substituted by one or more radicals, which are identical or different, chosen from
phenyl,
alkoxycarbonyl,
acyl, and
cyano radicals; and (a) R" denotes a methyl radical; and Z' denotes a radical —CHO, COR$_2$, —COOR$_3$, —CONR$_4$R$_5$, —CN, —SO$_2$R$_6$ or NO$_2$; or (b) R' and R" together form a radical —(CH$_2$)$_n$— in which n is as hereinbefore defined and Z' is as hereinbefore defined; or (c) R' is as hereinbefore defined and R" and Z' together form a radical —CO—(CH$_2$)$_p$— or —COO(CH$_2$)$_p$— in which p is as hereinbefore defined and the carbonyl group is attached in the position of Z'; the aforesaid saturated hydrocarbon radicals containing 1 to 20 carbon atoms each, the said unsaturated hydrocarbon radicals containing 2 to 20 carbon atoms each, and the radicals R$_1$, R$_2$, R$_3$, R$_4$, R$_5$ and R$_6$ each denote alkyl radicals containing 1 to 4 carbon atoms each and the alkyl moieties of the alkoxy-carbonyl radicals contain 1 to 4 carbon atoms each;

by treatment with an alkali metal alcoholate or an alkali or alkaline-earth metal carbonate in an organic solvent and with a halogenating agent at a temperature of from $-30°$ to $100°$ C.

2. A process according to claim 1, in which an alkali metal alcoholate derived from an alcohol of formula

in an organic solvent is used.

3. A process according to claim 2, in which the alkali metal alcoholate is sodium methylate or sodium ethylate.

4. A process according to claim 1, in which an alcohol of formula:

in the presence of sodium hydroxide or potassium hydroxide is used.

5. A process according to claim 2, in which the organic solvent is an alcohol of formula R$_1$OH toluene, ethyl ether, dimethylformamide or N-methylpyrrolidone.

6. A process according to claim 1, in which an alkali or alkaline-earth metal carbonate in an organic solvent chosen from acetone and acetonitrile is used.

7. A process according to claim 1, in which the halogenating agent is a molecular halogen, an N-halosuccinimide, sulphuryl chloride, or hexachloroethane.

* * * * *